United States Patent
Lage et al.

(10) Patent No.: US 10,390,775 B2
(45) Date of Patent: Aug. 27, 2019

(54) INTER-DETECTOR SCATTER ENHANCED EMISSION TOMOGRAPHY

(71) Applicants: Eduardo M. Lage, Boston, MA (US); Joaquin Lopez Herraiz, Brookline, MA (US); Vicente Jose Parot, Cambridge, MA (US); Shivang R. Dave, Rancho Cordova, CA (US)

(72) Inventors: Eduardo M. Lage, Boston, MA (US); Joaquin Lopez Herraiz, Brookline, MA (US); Vicente Jose Parot, Cambridge, MA (US); Shivang R. Dave, Rancho Cordova, CA (US)

(73) Assignee: Massachusetts Institute of Technology, Boston, MA (US)

( * ) Notice: Subject to any disclaimer, the term of this patent is extended or adjusted under 35 U.S.C. 154(b) by 1016 days.

(21) Appl. No.: 14/440,927

(22) PCT Filed: Nov. 7, 2013

(86) PCT No.: PCT/US2013/068858
§ 371 (c)(1),
(2) Date: May 6, 2015

(87) PCT Pub. No.: WO2014/074666
PCT Pub. Date: May 15, 2014

(65) Prior Publication Data
US 2015/0289825 A1    Oct. 15, 2015

Related U.S. Application Data

(60) Provisional application No. 61/723,465, filed on Nov. 7, 2012.

(51) Int. Cl.
*A61B 6/03* (2006.01)
*G01T 1/29* (2006.01)
(Continued)

(52) U.S. Cl.
CPC ............ *A61B 6/037* (2013.01); *A61B 6/4241* (2013.01); *A61B 6/5205* (2013.01);
(Continued)

(58) Field of Classification Search
CPC ..... G01T 1/2985; A61B 6/037; A61B 6/4216; A61B 6/4241; A61B 6/4258;
(Continued)

(56) References Cited

U.S. PATENT DOCUMENTS

| 8,530,846 B2 | 9/2013 | Cook et al. |
| 8,716,669 B2 * | 5/2014 | Miyaoka ............... G01T 1/2985 250/362 |

(Continued)

OTHER PUBLICATIONS

Lage et al. "Recovery and normalization of triple coincidences in PET." Med. Phys. 42 (3), Mar. 2015, pp. 1398-1410. (Year: 2015).*

(Continued)

*Primary Examiner* — Angela M Hoffa
(74) *Attorney, Agent, or Firm* — Quarles & Brady LLP

(57) ABSTRACT

A method and system for acquiring a series of medical images includes receiving medical imaging data corresponding to photons emitted from a subject having received a dose of a radiotracer. Determining, from the medical imaging data, coincidence events including photon coincidence events involving two photons and photon coincidence events involving more than two photons. The photon coincidence events involving two photons and photon coincidence events involving more than two photons are processed and use to reconstruct a series of medical images of the subject.

21 Claims, 4 Drawing Sheets

(51) Int. Cl.
    *G06T 11/00*     (2006.01)
    *A61B 6/00*     (2006.01)

(52) U.S. Cl.
    CPC .......... *G01T 1/2985* (2013.01); *G06T 11/005* (2013.01); *A61B 6/4216* (2013.01)

(58) Field of Classification Search
    CPC ........... A61B 6/5205; A61B 6/03; A61B 6/00; G06T 1/2985; G06T 11/005
    USPC ................................................. 600/425, 431
    See application file for complete search history.

(56) References Cited

U.S. PATENT DOCUMENTS

| | | | | |
|---|---|---|---|---|
| 9,223,747 | B2* | 12/2015 | Chuang | G06F 17/00 |
| 9,734,600 | B2* | 8/2017 | Berker | A61B 6/037 |
| 10,064,587 | B2* | 9/2018 | Liang | G01T 1/2985 |
| 10,215,864 | B2* | 2/2019 | Herraiz | G01T 1/1647 |
| 2009/0224158 | A1 | 9/2009 | Haselman et al. | |
| 2009/0274265 | A1* | 11/2009 | Koehler | G01N 23/046 378/15 |
| 2011/0150181 | A1* | 6/2011 | Cook | G01T 1/1648 378/86 |
| 2012/0138804 | A1 | 6/2012 | Miyaoka et al. | |
| 2012/0153165 | A1* | 6/2012 | Ott | G01T 1/2935 250/362 |
| 2012/0290519 | A1* | 11/2012 | Fontaine | G01T 1/2985 706/20 |
| 2014/0039831 | A1* | 2/2014 | Chuang | G06F 17/00 702/181 |
| 2015/0185339 | A1* | 7/2015 | Lage | G01T 1/2985 600/425 |
| 2015/0192685 | A1* | 7/2015 | Griesmer | G01T 1/1647 250/362 |
| 2016/0131774 | A1* | 5/2016 | Lage | A61B 6/481 600/426 |
| 2018/0116621 | A1* | 5/2018 | Berker | A61B 5/0035 |

OTHER PUBLICATIONS

International Search Report dated Apr. 8, 2014 in connection with PCT/US2013/068858.

Zanzonico, P., Positron Emission Tomography: A Review of Basic Principles, Scanner Design and Performance, and Current systems. Seminars in Nuclear Medicine, vol. XXXIV, No. 2 (Apr.), 2004; pp. 87-111 [online], [retrieved on Feb. 25, 2014]; Retrieved from the Internet <URL: http://www.sysf.physto.se/-kader/tomove/pet_principles_important.pdf>; entire document.

\* cited by examiner

INTER-DETECTOR SCATTER ENHANCED EMISSION TOMOGRAPHY

CROSS-REFERENCE TO RELATED APPLICATIONS

This application represents the national stage entry of PCT International Application No. PCT/US2013/068858 filed Nov. 7, 2013, which claims priority to U.S. Provisional Application Ser. No. 61/723,465, filed Nov. 7, 2012, the disclosures of which are incorporated by reference here in their entirety for all purposes.

STATEMENT REGARDING FEDERALLY SPONSORED RESEARCH

N/A

BACKGROUND OF THE INVENTION

The present invention relates to systems and methods for emission tomography and, more particularly, to systems and methods for inter-detector, scatter-enhanced positron emission tomography that provides an increase in the performance of current positron emission tomography scanners by allowing the counting of coincidences caused by inter-detector, scattered photons.

There are a variety of emission tomography imaging systems and methods. One clinically important example is positron emission tomography (PET), which, generally, utilizes an administered radionuclide to acquire two-dimensional and three-dimensional tomographic images of a target area or organ of interest in a subject. More specifically, such radionuclides are employed as radioactive tracers called "radiopharmaceuticals" by incorporating them into substances, such as glucose or carbon dioxide. These radiopharmaceuticals are then administered to the patient where they become involved in biological processes such as blood flow; fatty acid and glucose metabolism; and protein synthesis. Through a respective biological process, the radiopharmaceuticals accumulate in, or otherwise target, the area or organ of interest in the subject. By measuring or identifying photons emitted from the area or organ of interest by the accumulated or targeted radiopharmaceutical, clinically useful biological and physiological information can be acquired from the area or organ of interest.

For example, in PET, as the injected radioactive tracer decays, it emits positrons. The positrons travel a very short distance before they encounter an electron and, when this occurs, the positrons are annihilated and converted into two photons, or gamma rays. This annihilation event is characterized by two features that are pertinent to PET imaging. Namely, each gamma ray has an energy of 511 keV and the two gamma rays are directed in substantially opposite directions. An image is created by determining the number of such annihilation events at each location within the scanner's field of view.

To create such an image, typical PET scanners consist of one or more rings of detectors that are positioned to encircle the patient. Coincidence detection circuits connected to the detectors record only those photons that are detected simultaneously by two detectors located on opposite sides of the patient and that fall within an energy acceptance window around 511 keV. The number of such simultaneous events indicates the number of positron annihilations that occurred along a line joining the two opposing detectors. Within a few minutes, hundreds of millions of events can be recorded to indicate the number of annihilations along lines joining pairs of detectors in the ring. These numbers are employed to reconstruct an image using well-known tomographic reconstruction techniques.

For example, current clinical (and most preclinical) PET scanners and systems include a ring of block detectors for detecting emitted photons, typically in circular, such as the array shown in FIG. 1, or in hexagonal or octagonal arrays. Block detectors include a piece of scintillator material that converts the energy deposited by gamma rays into visible light. The scintillator material is usually segmented into many scintillation crystal elements configured in an array, which is read out by a number of individual photo-multiplier tubes (PMTs) or a position-sensitive photo-multiplier tube (PS-PMT) that convert the light emitted by the scintillation material into electrical signals having a magnitude proportional to the energy deposited by the gamma rays in the scintillator material. By combining the output signal of the PMTs or PS-PMT of the block detector, it is possible to determine the single crystal in which the detected photon interacted and the energy deposited by such photon.

Although block detectors have been demonstrated as the most cost-effective solution for the implementation of PET scanners, these detectors also present some drawbacks. For example, since each detector element is a block, if several photons interact simultaneously on the same block and the added energy of those photons is within a predefined energy acceptance window (around 511 keV), it is not possible to determine from the output signals of the detector if they were produced by the interaction of a single photon (thereby presenting useful information) or by the interaction of multiple photons (thereby presenting distorted or non-useful information).

In addition, as shown in FIG. 1, the ring of block detectors of a PET scanner includes individual detectors that are operated in coincidence with a fan beam of block detectors on the opposite side of the ring. The inner circle formed by edges of all such fan beams defines the useful field of view. Data is usually recorded simultaneously for all possible fan beams, and the PET scanner will produce an output whenever two photons are detected in opposite block detectors of a fan beam within a specified coincidence timing window (for example, in the range of hundreds of picoseconds to tens of nanoseconds) and when both events fall into a predetermined energy window (511 keV±$\Delta E$, where $\Delta E$ is a function of the energy resolution of the block detectors). Any such events are called prompt coincidences, but can be of three specific types: true coincidences, scatter coincidences, and random coincidences.

True coincidences occur when two photons produced from the same annihilation are detected within the time and energy windows of the system, as shown in FIG. 2A. Scatter coincidences occur when at least one of the photons undergoes scattering in the object under study, such as Compton scattering, where the photon loses a fraction of its total energy in the scatter interaction with the object before its detection. The scatter coincidence is, thus, detected in a pair of detectors that are non-collinear with the originating annihilation, as shown in FIG. 2B. Random coincidences, also known as accidental coincidences, occur when annihilation photons from two unrelated positron annihilation events are detected in opposite detectors, as shown in FIG. 2C. True coincidences produce valid information, while both scatter coincidences and random coincidences produce distorted information. In particular, scatter and random coincidences yield incorrect positional information, as shown by the dotted lines in FIGS. 2B and 2C, and contribute to a relatively uniform background noise in the resulting image, which results in a loss of contrast.

With respect to scatter coincidences, such events are typically assumed to occur only due to scattering within the patient, as shown in FIG. 2B, and current PET systems include scatter correction procedures based on this assumption. However, there are a large number of events in which Compton scattering occurs in the block detectors of the scanner, as shown in FIGS. 3A and 3B, depositing a fraction of the total energy of the photon in each interaction. In particular, FIG. 3A illustrates a scatter event where one of the photons from an annihilation event (photon A) interacts by photoelectric effect depositing energy in a detector within the acceptance energy window of the scanner (that is, 511 keV±ΔE), and the other photon (photon B) interacts by Compton scattering in another detector. Photon B deposits some of its energy in the detector it is incident upon, and the scattered photon (photon C) produced by the Compton scattering event deposits energy in another detector. FIG. 3B illustrates a scatter event where one of the photons from an annihilation event (photon A) interacts by photoelectric effect depositing energy in a detector within the acceptance energy window of the scanner, and the other photon (photon B) interacts by Compton scatter in another detector, where it deposits some of its energy, with the scattered photon (photon C) escaping from the detector ring.

In current clinical and preclinical PET scanners that include block detectors, no viable information is used from the scatter events shown in FIG. 3A because multiple detections are not identified by the coincidence system. That is, such events are rejected. Scatter events shown in FIG. 3B (that is, crystal scatter coincidences with two detection events) may be detected and processed in the same fashion as scatter events that have undergone scattering in the object (as shown in FIG. 2B). Thus, the data collected for events comprising more than two detections is thrown out and only data from prompt coincidences (including true coincidences, in-body scatter coincidences, random coincidences, and crystal scatter coincidences with two detection events) are used to compose images. This limits the potential sensitivity of the system and quality of the resulting images.

Approaches have been presented to make use of inter-detector scatter events (in particular, events as shown in FIG. 3A); however, such approaches have only been proposed using non-standard detector configurations, such as Compton cameras or high granularity detectors, and cannot be used with conventional block-detector type PET scanners. Such non-standard detectors can be very expensive and the corresponding systems must be combined with complicated mathematical models. Furthermore, some of these systems require the use of inter-detector scatter data to perform within the same range as those obtained in block detector-based scanners that do not use such data. Thus, although these non-standard detectors may be capable of detecting inter-detector scatter events, they do not produce higher quality images than traditional block-detector type PET.

For example, a Compton camera is a radiation detector that is usually composed of two detection planes, commonly made from semiconductor materials, which provide better energy resolution than radiation detectors using typical scintillation crystals. Photons emitted from a source are scattered in the first plane through Compton scattering and are absorbed in the second plane through photoelectric effect. In both planes, the position of the interaction and the energy deposited are measured. The detectors are operated in coincidence, so that only photons that interact with both detector-planes and deposit a total energy within a given window are recorded. In this case, and due to the disposition of the detectors, it is improbable that the first interaction would be detected in the second detector plane. Both the energy of the initial photon and the energy deposited in the first detector are known, and therefore the scattering angle can be calculated using the Compton formula. This defines a conic surface in which the origin of the initial photon is contained. The precision of this calculation is strongly related to the energy resolution of the detector being used for the construction of the Compton camera. The real location of the source is obtained as the intersection point of several of these conic surfaces. When several point sources or a continuous source distribution are imaged (for example, an organ containing a radioisotope), the reconstruction becomes more challenging, resulting in this type of device usually providing images of poor quality in comparison to traditional PET images.

In another example, scanners with high granularity detectors (detectors that, unlike block detectors, require that each detection element be read-out independently) are expensive and computationally complex. More specifically, an objective of such high-granularity detector systems is to determine the sequence of interaction points of each photon (for example, the first interaction point, the second interaction point, etc.) to find the appropriate line of response in a multiple coincidence event. For example, given the example of FIG. 3A, such systems must determine whether the first photon in the inter-detector scatter event was photon B (thereby illustrating an annihilation response line along A-B), or photon C (thereby illustrating an annihilation response line along A-C). These determined lines of response from multiple coincidence events are then combined with true coincidence lines to compose images. One system in particular requires the use of three-dimensional high-granularity semiconductor detectors. Unlike scintillation crystals used in block detectors, semiconducting detectors, such as cadmium zinc telluride (CZT), directly sense the ionization signal created by the annihilation photon absorption. CZT detectors have good energy resolution, but their stopping power for 511 keV is lower than most scintillation crystals, and the timing resolution is much worse than what can be achieved with block detectors. Furthermore, the composition of the semi-conductor detector and detection system design cause a large fraction of all photons (around 94%) undergo inter-detector scattering. For this reason, the ability to correctly position inter-detector scatter events strongly determines the performance of such a system. This results in a high price and high complexity of such scanners with little improvement in performance in comparison to block detector-type scanners, which can rely heavily on true coincidence events. As a result, to date, high-granularity camera scanners cannot compete with the performance and cost-effectiveness of block detector-type scanners.

Thus, current approaches for utilizing inter-detector scatter events require non-conventional scanners that are more expensive, are more computationally complex, and cannot, generally, achieve higher-quality images than current conventional block-detector scanners. Furthermore, the methods developed for interpreting and recording inter-detector scatter events using non-conventional scanner approaches cannot practically be applied to conventional block-detector scanners due to their inherent precision and performance characteristics.

Therefore, it would be desirable to have a system and method for block detector-based PET imaging that has increased sensitivity, such as by using data collected from inter-detector scatter events.

SUMMARY OF THE INVENTION

The present invention overcomes the aforementioned drawbacks by providing a system and method for emission tomography, such as positron emission tomography (PET), that enables the use of data from inter-detector scatter events (that is, three or more photon coincidence events) during image reconstruction. Thus, the present invention provides an improvement in scanner performance, due to the use of both traditional true coincidence data as well as inter-detector scatter coincidence data. This configuration can be adopted in existing preclinical and clinical PET scanners without requiring additional or other non-conventional detector elements.

In accordance with one aspect of the present invention, an emission tomography system is provided for acquiring a series of medical images of a subject. The system includes a bore configured to receive the subject having been administered a dose of a radiotracer and a detector system having a field of view and arranged about the bore configured to receive gamma rays emitted from the subject as a result of the dose of the radiotracer and communicate signals corresponding to the gamma rays. The system also includes a data processing system configured to receive the signals from the detector system, determine, from the signals, photon coincidence events involving two photons and apply a set of predetermined factors to determine, from the signals, photon coincidence events involving more than two photons. The data processing system is also configured to sort the photon coincidence events involving two photons along projected lines of response in the field of view and sort and weight the photon coincidence events involving more than two photons along projected lines of response based at least on the sorted photon coincidence events involving two photons. The system also includes a reconstruction system configured to receive the sorted photon coincidence events involving two photons and the sorted photon coincidence events involving at least three photons from the data processing system and reconstruct therefrom a series of medical images of the subject.

In accordance with another aspect of the present invention, a method for acquiring a series of medical images of a subject having received a dose of a radiotracer is provided. The method includes acquiring imaging data from a detector system configured to receive photons emitted from the subject as a result of receiving the dose of the radiotracer and determining, from the imaging data, photon coincidence events involving two photons. The method also includes applying a set of predetermined factors to determine, from the signals, photon coincidence events involving more than two photons and sorting the photon coincidence events involving two photons along projected lines of response in the field of view. The method further includes sorting and weighting the photon coincidence events involving more than two photons along projected lines of response based at least on the sorted photon coincidence events involving two photons and reconstructing an image of the subject using the sorted photon coincidence events involving two photons and the sorted and weighted photon coincidence events involving at least three photons.

In accordance with yet another aspect of the present invention, a positron emission tomography system is disclosed for acquiring a series of medical images of a subject. The system includes a plurality of scintillator-type block detectors arranged about a bore configured to receive the subject and to acquire gamma rays emitted from the subject as a result of a radiotracer administered to the subject and configured to communicate signals corresponding to acquired gamma rays. The system also includes a data processing system configured to receive the signals from the plurality of detectors, identify temporal information and energy information of photons of the acquired gamma rays, and determine photon coincidence events involving two photons. The data processing system is also configured to determine photon coincidence events involving at least three photons using the temporal information and energy information. The data processing system is further configured to sort the photon coincidence events involving two photons along projected lines of response in a field of view of the subject and sort the photon coincidence events involving at least three photons along projected lines of response based on the sorted photon coincidence events involving two photons. The system also includes a reconstruction system configured to receive the sorted photon coincidence events involving two photons and the sorted photon coincidence events involving at least three photons from the data processing system and reconstruct therefrom a series of medical images of the subject.

In accordance with still another aspect of the present invention, a method is disclosed for acquiring a series of medical images of a subject. The method includes detecting photons emitted from the subject in response to a radiotracer having been administered to the subject, creating imaging data based on the detected photons, and processing the imaging data to identify temporal information including coincidence events and energy information associated with the detected photons. The method also includes assigning the imaging data corresponding to photon coincidence events involving two photons and photon coincidence events involving at least three photons into datasets based on the temporal information and the energy information and sorting the photon coincidence events involving two photons into an image array. The method further includes sorting the photon coincidence events involving at least three photons into the image array based on the sorted photon coincidence events involving two photons and reconstructing a series of medical images of the subject from the image data array.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE DISCLOSURE

The present invention recognizes that one of the greatest strengths of emission tomography, such as positron emission tomography (PET), is its sensitivity to true events (that is, events that provide correct information to generate an image). The sensitivity of a PET scanner is determined primarily by the absorption efficiency of the detector system and its solid angle coverage of the imaged object. Increasing the sensitivity of a PET scanner can permit, among other things, a reduction in scan time or an equivalent reduction in the amount of radioactive compound used to obtain similar quality images. However, since most commercial PET systems use similar material for detectors, which is the most expensive component of PET systems, the only current method to increase sensitivity is to increase the detector volume, thereby increasing the complexity and price of the system. As will be described, the present invention overcomes these drawbacks by providing a system and method for positron emission tomography that allows increased system sensitivity and image quality without additional hardware requirements.

Figure 4:
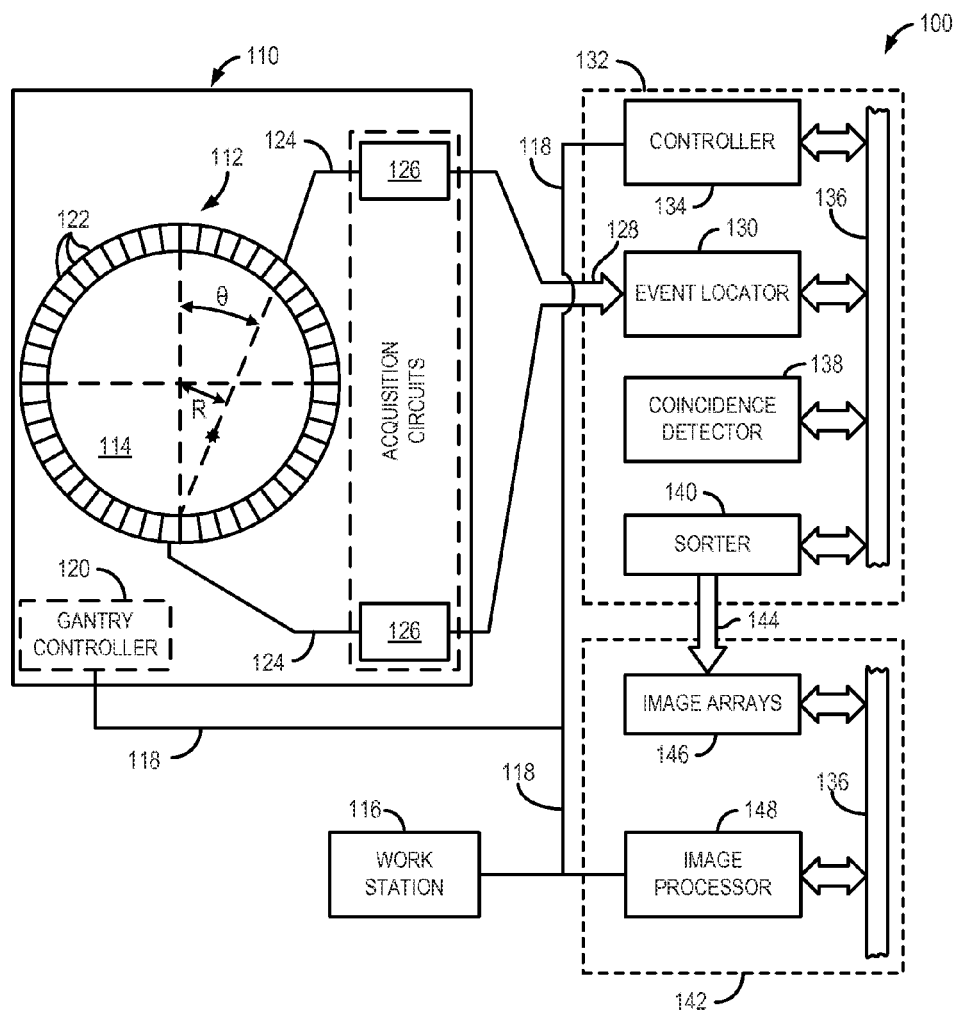
FIG. 4 is a schematic view of a PET system in accordance with the present invention.

Referring particularly to FIG. 4, a positron emission tomography system 100 for use with the present invention is illustrated. As shown in FIG. 4, the PET system 100 includes an imaging hardware system 110 that includes a detector ring assembly 112 about a central axis, or bore 114. An operator work station 116 communicates through a communications link 118 with a gantry controller 120 to control operation of the imaging hardware system 110.

The detector ring assembly 112 is formed of a multitude of radiation block detector units 122. Each radiation block detector unit 122 includes a set of scintillator crystals that is disposed in front of an array of photomultiplier tubes or a position-sensitive photomultiplier tube (not shown). Each photomultiplier tube produces a signal responsive to detection of a photon on communications line 124 when a scintillation event occurs. A set of acquisition circuits 126 receive the signals and produce signals indicating the event coordinates (x, y) and the total energy associated with the photons that caused the scintillation event. These signals are sent through a cable 128 to an event locator circuit 130. Each acquisition circuit 126 also obtains information from the detector's signals that indicates the exact moment the scintillation event took place. For example, sophisticated digital electronics can obtain this information regarding the precise instant in which the scintillations occurred from the samples of the signals used to obtain energy and event coordinates.

The event locator circuits 130 in some implementations, form part of a data acquisition processing system 132 that processes the signals produced by the acquisition circuits 126. The data acquisition processing system 132 usually includes a general controller 134 that controls communications for example, by way of a backplane bus 136, and on the general communications network 118. The event locator circuits 130 assemble the information regarding each valid event into a set of numbers that indicate precisely when the event took place, the position in which the event was detected and the energy deposited by the photon. This event data packet is conveyed to a coincidence detector 138 that is also part of the data acquisition processing system 132.

Figure 2A:
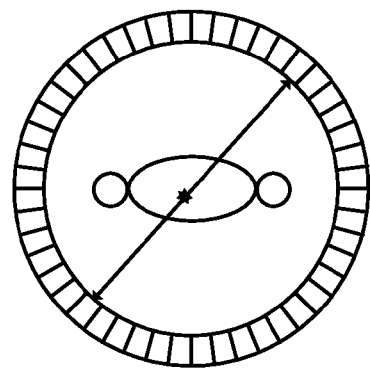
FIGS. 2A-2C are schematic views of prompt coincidence events in a PET system, including a true coincidence event (FIG. 2A), a scatter coincidence event (FIG. 2B), and a random coincidence event (FIG. 2C).
Figure 1:
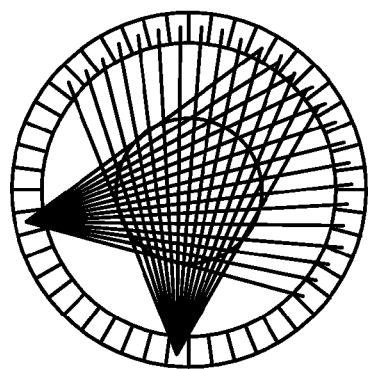
FIG. 1 is a schematic view of a ring of block detectors in a positron emission tomography (PET) system.
Figure 2B:
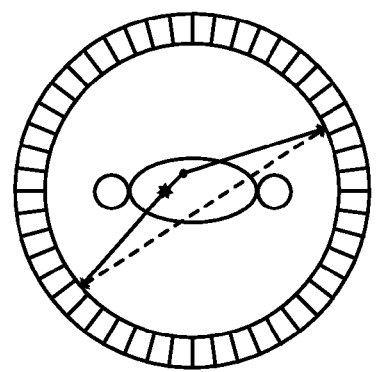
Figure 2C:
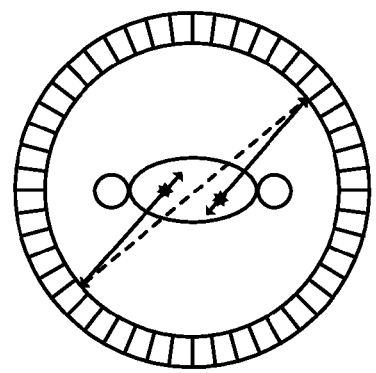

The coincidence detector 138 accepts the event data packets from the event locator circuit 130 and determines if any two of them are in coincidence. Coincidence is determined by a number of factors. First, the energy associated with each event data packet must fall within a predefined energy acceptance window, such as around 511 keV±ΔE (where ΔE is a function of the energy resolution of the block detectors). Second, the time markers in each event data packet must be within a predetermined time window, for example, 5 nanoseconds or even down to picoseconds. Third, the locations indicated by the two event data packets must lie on a straight line that passes through the field of view in the scanner bore 114. Coincidences that fall under these factors can be considered prompt coincidences, including true coincidences (as shown in FIG. 2A), in-body scatter coincidence (as shown in FIG. 2B), and random coincidences (as shown in FIG. 2C). Traditionally, events that cannot be paired are discarded from consideration by the coincidence detector 138, but coincident event pairs are located and recorded as a coincidence data packet. This coincidence data packet, which constitutes traditional PET data, will be referred to as dataset 1.

In accordance with the present invention, the coincidence detector 138 may perform the above-described functionality of a traditional PET system, but can also determine if any three or more event data packets are in coincidence (that is, as a multiple coincidence event such as an inter-detector scatter coincidence), as further described below. These multiple coincidence events can then be located and recorded as another coincidence data packet, which will be referred to as dataset 2.

Dataset 1, dataset 2, and other acquired data (including non-coincidence data and/or data corresponding to photon events with energy deviating from the standard 511 keV of an electron-positron annihilation event) are provided to a sorter 140. The function of the sorter in many traditional PET imaging systems is to receive the coincidence data packets and generate memory addresses from the coincidence data packets for the efficient storage of the coincidence data. In that context, the set of all projection rays, or lines of response, that point in the same direction (θ) and pass through the scanner's field of view (FOV) is a complete projection, or "view". The distance (R) between a particular line of response and the center of the FOV locates that line of response within the FOV. The sorter 140 counts all of the events that occur on a given line of response (R, θ) during the scan by sorting out the coincidence data packets that indicate an event at the two detectors lying on this line of response. Because multiple coincidence events involve more than two detectors, such events may be counted on one or more given lines of response (that is, a subset of lines of response) based at least on the count of prompt coincidence events on those lines of response, as further described below. Once all events are counted, the coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 140 counts all events occurring along each line of response (R, θ) and organizes them into an image data array. As further described below, dataset 1 and dataset 2 can be organized into a single image dataset array.

The sorter 140 provides the image dataset array to an image processing/reconstruction system, for example, by way of a communications link 144 to be stored in an image array 146. The image array 146 holds the dataset array for access by an image processor 148 that reconstructs one or more images corresponding to the dataset array.

Figure 5:
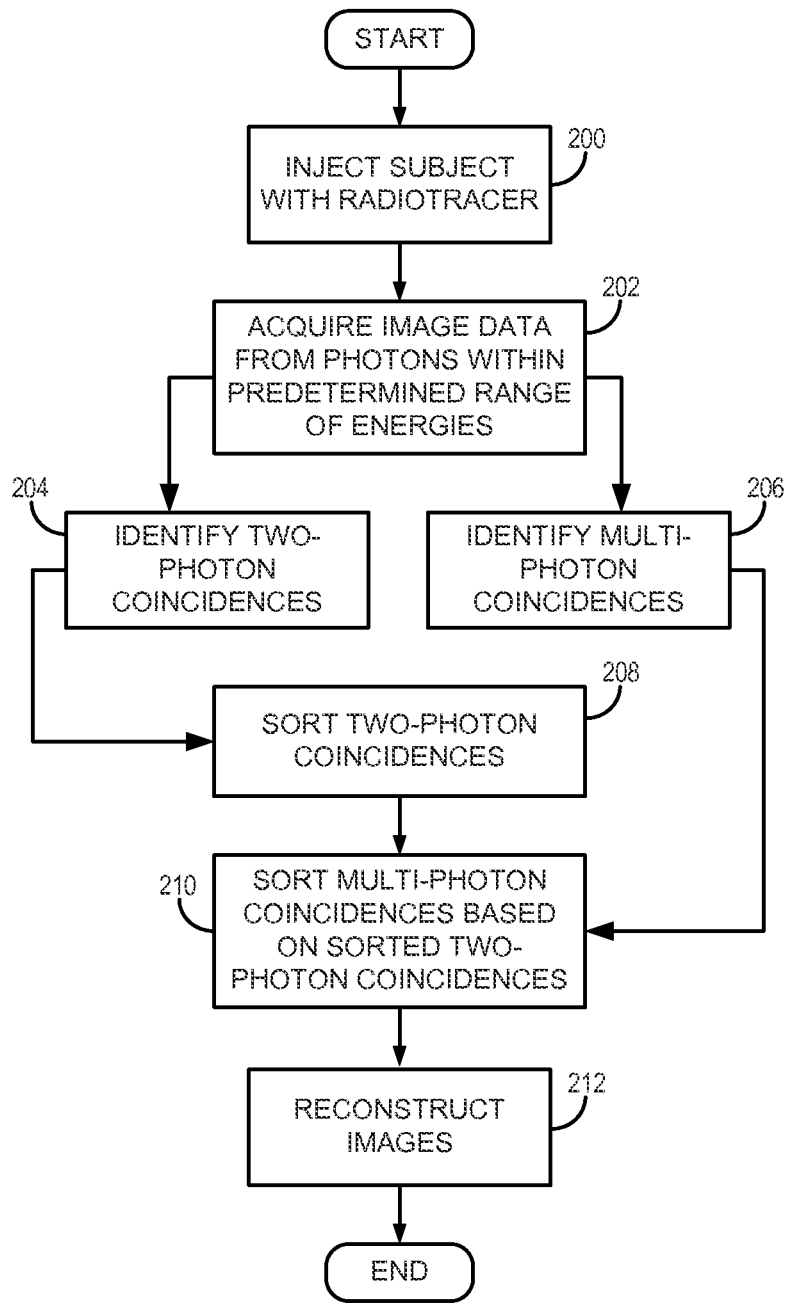
FIG. 5 is a flow chart setting forth the steps of a method of using a PET system in accordance with the present invention.

Referring now to FIG. 5, and with reference to the PET system 100 described above, a process for acquiring image data and creating images in accordance with the present invention will be described. More specifically, FIG. 5 illustrates a process for inter-detector scatter enhanced PET. Though described with reference to the PET system 100, this process may be executed on any conventional PET system with scintillator-type block detectors. This process may also be executed in PET systems using high-granularity detectors. Generally, the process begins at process block 200 with the administration of a radiotracer labeled with a radioisotope to a subject, followed by process block 202 with the acquisition of image data. Next, at process blocks 204 and 206, two-photon coincidences and three-or-more-photon coincidences, respectively, are identified. As used herein "multi-photon" or "multiple-photon" coincidences will refer to coincidences including more than two photons. As discussed above, two-photon coincidences can be considered traditional "prompt coincidences," while multiple-photon coincidences are indicative of other events such as "inter-detector scatter coincidences." At process block 208, the prompt coincidences are sorted and mapped, and at process block 210, the multiple photon coincidences are sorted and mapped based on at least the prompt coincidences sorted in process block 208. At process block 212, a set of images is reconstructed based on the sorted prompt coincidence data as well as the sorted multiple photon coincidence data.

Figure 3A:
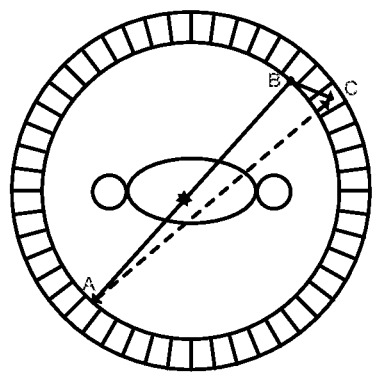
FIGS. 3A-3B are schematic views of inter-detector scatter coincidence events in a PET system.
Figure 3B:
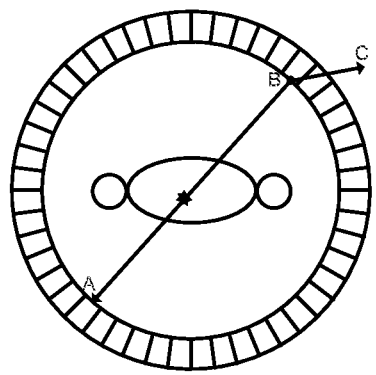

More specifically, with respect to process block 202, image data is acquired by detecting and recording N-photon coincidences within a "wide" coincidence window. For example, the wide coincidence window is a predetermined window that may be on the order of picoseconds to nanoseconds, in different detectors of the scanner, and across a predetermined range of energies. That is, a wide range of image data is collected to ensure that data for each photon event, including inter-detector scattered photons that deposit energies below the standard 511 keV, is acquired. In other words, in order to detect and register inter-detector scatter events (that is, to accept three or more photon coincidences), a PET scanner in accordance with the present invention is configured to employ a wider energy acceptance window than the one commonly used in clinical and preclinical scanners. Since the energy window in current scanners is a narrow band centered at 511 keV, events like the one shown in FIG. 3A are traditionally discarded by the software or hardware of the scanner because, although the detected photon A has an appropriate energy, generally neither photon B nor photon C is within the energy acceptance window. With reference to the PET system 100 described above, process block 202 can be executed by the acquisition circuits 126 and the event locator circuits 130 assembling detection signals produced by detector units 122 into event data packets that indicate when each event took place, the position in which each event was detected, and the energy deposited by each event.

At process block 204 and process block 206, two-photon coincidences and multiple-photon coincidences, respectively, are identified. Two-photon coincidences can be detected by a conventional set of factors, as described above, while three-photon coincidences (or other multiple photon coincidences) can be detected by a separate set of factors. For the sake of clarity, a three-photon coincidence, or triple coincidence, event will be described herein; however, the following description can be applied to four-photon, five-photon . . . , n-photon coincidences. The set of factors used to detect triple coincidences can include some factors similar to those required for coincident event pairs. For example, a set of factors may constrain time markers in each event data packet to be within a predetermined time window, such as 5 nanoseconds or even down to picoseconds, and the locations. The constrained locations may be indicated by at least the two of the three event data packets being on a straight line that passes through the field of view. However, the following additional factors may be used for triple coincidences, but are not necessary for traditional coincidence pairs.

First, for 511 keV gamma rays which interact by Compton scattering, the deviation of the resulting photon from the original trajectory or scattering angle may be constrained to be small (for example, between 0 and 60 degrees) and with a high probability. Therefore, referring to the example inter-detector scatter event of FIG. 3A, if the residual scattered photon is also detected (photon C), it will be most likely detected in a block detector close to the one that received the first interaction (photon B). Often, this detector in a common scanner will also belong to the fan beam of detectors in coincidence with the one which detected the interaction of photon A. Second, the sum of the energies of photons B and C may be constrained to equal 511 keV±ΔE and the energy of photon A may be required to be within a range equal to 511 keV±ΔE to assure that this photon interacted by photoelectric effect. Observed triple coincidences that fulfill these criteria additional or any combination of criteria can be considered inter-detector scatter events.

With reference to the PET system 100 described above, process blocks 204 and 206 can be executed by the coincidence detector 138, where data event packets are accepted, analyzed, and prompt coincidences are recorded in a first coincidence data packet, referred to as dataset 1, and multiple photon coincidences are recorded in a second coincidence data packet, referred to as dataset 2.

At process block 208, the prompt coincidences (also considered double coincidences) are sorted and mapped along their respective lines of response in accordance with conventional sorting methods, as described above. At this point, it is possible to apply standard corrections to the double coincidence data, such as scatter or random corrections, in order to increase the signal to noise ratio (that is, true coincidences compared to the sum of in-body scattered and random coincidences). The present invention can be used to sort "triple random" events. Triple random events are events in which three photons are detected simultaneously and two of the photons come from the same positron-electron annihilation and the third one from a different positron-electron annihilation. For example, the criteria for determining a "triple random" event may be determining a collection of three photons that are within a predetermined energy window around 511 keV. For example, a predetermined energy window may be defined as approximately 511 keV±ΔE.

At process block 210, the multiple photon coincidences are sorted and mapped based on at least the coincidences sorted in process block 208. More specifically, given the example shown in FIG. 3A, at this time during processing, it is still uncertain which interaction (that is, photon B or photon C) was first in the inter-detector scatter. Thus, there are three possible lines of response along points A, B, and C, although, in this example line B-C would not be used as a possible line of response because it does not pass through the field of view (which could be one of the factors/criteria, as discussed above). Traditional, state-of-the-art radiation detectors do not have sufficient timing resolution to determine the first interaction event from the time measurements, and therefore there is an uncertainty to determine if the appropriate line is A-B or A-C.

For this reason, the present invention can store and sort multiple-photon coincidences separate from double coincidences. The information gathered from the double coincidence events, which are already sorted, can then be used as a reference to distribute the inter-detector scatter events along appropriate lines of response. In the simplest case and continuing with the example of FIG. 3A above, if a number of inter-detector scatter events is detected between locations A-B-C, and these locations have a subset of valid lines of response to which distribute the inter-detector scatter events (that is, lines A-B and A-C), the number of inter-detector scatter events assigned to each line of response in the subset can be determined by a linear combination between: (a) the number of inter-detector scatter events detected between locations A-B-C; and (b) a metric obtained from the number of double coincidence events for each line of response in the subset. An example of this metric is the number of prompt coincidence events detected in each line of response in the subset. Another example of the metric is the number of prompt coincidence events detected in the block detector pair to which each line of response in the subset belongs. These metrics can be refined using, among other data, information about the energy deposited by each photon (B and C) and their corresponding scattering angle based on the Klein-Nishina formula for scatter photons.

In a basic example, the number of double coincidence events on each possible line of response in a subset is used to determine the probability of a multiple coincidence event actually occurring on each possible line of response. These probabilities are then used to wholly or partially distribute a weighted coincidence event along each respective line of response. More specifically, if the ratio of prompt responses at line A-B to line A-C is 1:1, the triple coincidence will add 0.5 to the coincidence count on line A-B, and 0.5 to the coincidence count on line A-C. However, if the ratio of true responses at line A-B to line A-C is 0:1, the triple coincidence will add 0 to the coincidence count on line A-B, and 1 to the coincidence count on line A-C.

These basic examples can include any other criteria discussed above to refine and improve the assigned probabilities for distributing of the events. In addition, a number of further improvements based on internal characteristics of the scanners, such as the timing resolution of scanners with time-of-flight (TOF) capability, can also be used to refine the assigned probabilities. Thus, multiple-photon coincidence counts can be distributed across the valid lines of response given the prompt coincidence counts-based probability of occurring along each line of response, timing, energy deposited, amongst other potential criteria.

With reference to the PET system 100 described above, process blocks 208 and 210 can be executed by the sorter 140, where dataset 1 and dataset 2 are accepted, dataset 1 is analyzed and events occurring along each line of response are counted according to conventional methods, and dataset 2 is analyzed and events are distributed along all valid lines of response based on at least the events in dataset 1 as well as the additional criteria discussed above. All counted events along the lines of response from dataset 1 and dataset 2 may then be organized into a common image dataset array to be stored in an image array 146.

At process block 212, a set of images is reconstructed, where the images are based on both double coincidence data as well as multi-photon or inter-detector scatter coincidence data. With reference to the PET system 100 described above, process block 212 can be executed by the image processor 148, where the image dataset array, held by the image array 146, is processed and reconstructed into an image or a series of images corresponding to the image dataset array. The use of inter-detector scatter events during image reconstruction can result in images with an increased number of counts, and consequently, increased signal to noise ratio (SNR) and increased contrast to noise ratio (CNR). More specifically, because these additional events, which are determined from data that is traditionally thrown out, can be counted and used to reconstruct the images, an emission tomography system using this method has a higher sensitivity in comparison to conventional PET systems.

Thus, the method described herein provides an improvement in sensitivity that can be adopted in existing preclinical and clinical PET scanners without requiring any hardware modifications. For example, traditionally, performance parameters are very similar among commercially available PET scanners with similar hardware, and there is an almost linear trend between the quantity of detector material used in the scanner, its sensitivity, and its price. However, the present invention can provide a competitive advantage to current commercially available scanners, since sensitivity can be increased using data that is readily available without requiring additional materials and, thus, additional material costs. Depending on the scanner and patient size, the method of the present invention can provide more than a 15% increase in sensitivity compared to traditional PET images.

Since the proposed methods of the present invention do not require any specialized detectors to utilize multiple coincidence events such as inter-detector scatter events, the present invention can be implemented on any PET scanner, including those already available on the market. This is a significant advantage over other inter-detector scatter approaches that require expensive, non-standard detector configurations, such as Compton cameras or high granularity cameras. Furthermore, these non-standard detectors must be combined with complicated mathematical models to determine the first interaction point in a sequence of photon interactions within a detector (that is, to detect the correct line of response upon which the annihilation event occurred). The present invention, however, does not require such determinations. Rather, the present invention utilizes data from prompt coincidence events to distribute multiple coincidence events such as inter-detector scatter events as assigned probabilities across multiple lines of response. This requires minimal computation that results in a great increase in image quality.

Thus, the present invention provides a method and system to increase the sensitivity of current clinical and preclinical PET scanners by using multiple coincidences such as those caused by inter-detector scatter photons (that is, data that is normally discarded in current state-of-the-art scanners and PET technologies). As discussed above, this can be beneficial to commercial PET scanners by increasing sensitivity without increasing costs. Furthermore, this can be beneficial in research and clinical applications in which the sensitivity of the system traditionally limits the achievable performance. For example, applications with protocols that require kinetic modeling of tracers in which the measurement of the initial passage of the tracer must be determined, or protocols that require radiotracers labeled with very short half-life isotopes, could greatly benefit from a system with increased sensitivity without the concomitant requirement of increased scanning time.

The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. An emission tomography system for acquiring a series of medical images of a subject, the system comprising:
   a bore configured to receive the subject having been administered a dose of a radiotracer;
   a detector system having a field of view and arranged about the bore configured to receive gamma rays emitted from the subject as a result of the dose of the radiotracer and communicate signals corresponding to the gamma rays;
   a data processing system configured to:
      receive the signals from the detector system;
      determine, from the signals, photon coincidence events involving two photons;
      apply a set of predetermined factors to determine, from the signals, photon coincidence events involving more than two photons;
      sort the photon coincidence events involving two photons along projected lines of response in the field of view;
      sort and weight the photon coincidence events involving more than two photons along projected lines of response based at least on the sorted photon coincidence events involving two photons; and
   a reconstruction system configured to receive the sorted photon coincidence events involving two photons and the sorted photon coincidence events involving more than two photons from the data processing system and reconstruct therefrom a series of medical images of the subject.

2. The system of claim 1 wherein the set of predetermined factors include at least one of a predetermined time window, a location constraint, a scattering angle constraint, a predetermined energy window, and an energy sum constraint.

3. The system of claim 2 wherein the predetermined time window includes a temporal resolution of one of multiple nanoseconds and picoseconds, the location constraint includes a spatial window limited to straight lines extending through the field of view, the scattering angle constraint is between 0 degrees and 60 degrees, the predetermined energy window is approximately 511 keV±ΔE, and the energy sum constraint is approximately 511 keV±ΔE.

4. The system of claim 1 wherein weighting the photon coincidence events involving more than two photons includes applying a metric derived from the photon coincidence events involving two photons.

5. The system of claim 4 wherein the metric includes at least one of a number of photon coincidence events involving two photons detected in each line of response and a number of photon coincidence events involving two photons detected in a detector pair of the detector system to which each line of response corresponds.

6. The system of claim 1 wherein sorting the photon coincidence events involving more than two photons includes sorting along the lines of response using a distribution of assigned probabilities based on a ratio of the photon coincidence events involving two photons along the lines of response.

7. The system of claim 1 further comprising a set of acquisition circuits for indicating event coordinates of a scintillation event.

8. The system of claim 7 further comprising a locator circuit for processing signals produced by the acquisition circuits.

9. The system of claim 8 further comprising a coincidence detector for accepting data packets from the locator circuit and determining if the data packets are in coincidence.

10. The system of claim 1 wherein the detector system comprises a plurality of scintillator-type block detectors.

11. The system of claim 1 wherein the photon coincidence events involving more than two photons are sorted along the projected lines of response based on timing information.

12. The system of claim 1 wherein the photon coincidence events involving more than two photons and the photon coincidence events involving two photons are determined by separate factors.

13. The system of claim 1 wherein the data processing system is further configured to identify temporal information and energy information of photons of the received gamma rays.

14. The system of claim 13 wherein identifying the temporal information includes applying a predetermined window having a temporal resolution of at least one of nanoseconds and picoseconds.

15. The system of claim 13 wherein the photon coincidence events involving more than two photons are sorted along the projected lines of response based on the sorted photon coincidence events involving two photons, the temporal information, and the energy information.

16. A positron emission tomography system for acquiring a series of medical images of a subject, the system comprising:
   a plurality of scintillator-type block detectors arranged about a bore configured to receive the subject and to acquire gamma rays emitted from the subject as a result of a radiotracer administered to the subject and configured to communicate signals corresponding to acquired gamma rays;
   a data processing system configured to:
      receive the signals from the plurality of detectors;
      identify temporal information and energy information of photons of the acquired gamma rays;
      determine photon coincidence events involving two photons;
      using the temporal information and energy information, determine photon coincidence events involving at least three photons;
      sort the photon coincidence events involving two photons along projected lines of response in a field of view of the subject;
      sort and weight the photon coincidence events involving at least three photons along projected lines of response based on the sorted photon coincidence events involving two photons; and
   a reconstruction system configured to receive the sorted photon coincidence events involving two photons and the sorted photon coincidence events involving at least three photons from the data processing system and reconstruct therefrom a series of medical images of the subject.

17. The system of claim 16 wherein identifying the temporal information includes applying a predetermined window having a temporal resolution of at least one of nanoseconds and picoseconds.

18. The system of claim 16 wherein the photon coincidence events involving at least three photons are sorted along the projected lines of response based on the sorted photon coincidence events involving two photons, the temporal information, and the energy information.

19. The system of claim 18 wherein the photon coincidence events involving at least three photons are sorted along the projected lines of response based on timing information.

20. The system of claim 16 wherein the photon coincidence events involving at least three photons are sorted along the projected lines of response using a distribution of assigned probabilities based on a ratio of the sorted photon coincidence events involving two photons along the projected lines of response.

21. The system of claim 16 wherein the photon coincidence events involving at least three photons and the photon coincidence events involving two photons are determined by separate factors.

\* \* \* \* \*